(12) United States Patent
Caillat et al.

(10) Patent No.: US 8,152,736 B2
(45) Date of Patent: Apr. 10, 2012

(54) DEVICE FOR CONTACT MOLECULAR SAMPLING

(75) Inventors: Patrice Caillat, Grenoble (FR); Franck Martin, Montpellier (FR); Marie-Line Cosnier, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 917 days.

(21) Appl. No.: 11/814,730

(22) PCT Filed: Feb. 2, 2006

(86) PCT No.: PCT/FR2006/050089
§ 371 (c)(1),
(2), (4) Date: Jul. 25, 2007

(87) PCT Pub. No.: WO2006/082344
PCT Pub. Date: Aug. 10, 2006

(65) Prior Publication Data
US 2010/0049083 A1    Feb. 25, 2010

(30) Foreign Application Priority Data
Feb. 2, 2005  (FR) ...................................... 05 50303

(51) Int. Cl.
*A61B 10/00* (2006.01)
(52) U.S. Cl. ...................................................... 600/562
(58) Field of Classification Search .................. 600/300, 600/562, 570, 572, 573, 575, 584; 351/200
See application file for complete search history.

(56) References Cited

U.S. PATENT DOCUMENTS

| | | | |
|---|---|---|---|
| 4,243,049 A | 1/1981 | Goodale et al. | |
| 4,700,713 A | 10/1987 | Kist | |
| 4,981,143 A | 1/1991 | Sakita et al. | |
| 5,133,361 A | 7/1992 | Cox et al. | |
| 6,138,766 A | 10/2000 | Finnerty et al. | |
| 6,607,494 B1 | 8/2003 | Fowler | |
| 2004/0181172 A1* | 9/2004 | Carney et al. | 600/573 |
| 2006/0068450 A1 | 3/2006 | Combette et al. | |

FOREIGN PATENT DOCUMENTS

EP  1 234 543 A1  8/2002
WO  WO 99/25251  5/1999

OTHER PUBLICATIONS

Surface-enhanced laser desorption/ionization, at http://en.wikipedia.org, accessed Mar. 3, 2011.
Katz et al, BJU Int'l., 2006, vol. 96, pp. 477-482.
Issaq et al, Anal. Chem., Apr. 2003, pp. 149A-155A.

* cited by examiner

*Primary Examiner* — Jeffrey G Hoekstra
(74) *Attorney, Agent, or Firm* — Oblon, Spivak, McClelland, Maier & Neustadt, L.L.P.

(57) ABSTRACT

A device (6) to sample molecules of biological interest is described. The device (6) includes capture zones (10) whose developed surface area is much greater than the surface so that sampling by contact allows a sufficient quantity of molecules to be obtained to achieve reliable analysis, whilst being sized so that the device (6) is neither invasive nor aggressive.
In particular, the device comprises tiered capture zones (10) located on a support (12) fabricated using microtechnology techniques; the capture zones (10) may advantageously be functionalised.

38 Claims, 5 Drawing Sheets

DEVICE FOR CONTACT MOLECULAR SAMPLING

TECHNICAL AREA

The invention concerns the area of non-invasive clinical diagnosis and/or treatment follow-up. More particularly, the invention relates to a microscopic sampling device to sample molecules of biological interest by contact, which does not require any ablation or biopsy and whose architecture is such that its insertion does not cause any damage to surrounding tissue. The invention is particularly suitable for proteomics or genomics.

The invention also concerns a method with which it is possible to determine the protein composition of the different layers of a tissue. In particular, this method is suitable for the mapping of tumours, e.g. brain tumours.

STATE OF THE PRIOR ART

In the same way as surgery is tending to be increasingly less invasive, clinical diagnosis and treatment follow-up techniques are tending towards miniaturisation of the tools needed for the various sampling and control operations.

Progress in imaging has largely contributed towards this development, in particular in cancerology, e.g. via two lines of approach: improvement in the detection limit of cancerous tumours, increase in surgical operation assistance through the systematic use of identification and positioning aid methodologies.

In parallel, molecular biology, whether at genomic or proteomic level, is increasingly more associated with diagnosis. In some cases for example it is envisaged to replace the anatomopathologist's eye by a molecular analysis method, and numerous developments are taking place in the areas of proteomics and associated mass analysis to identify and characterize biological markers.

Nevertheless the method of sampling target molecules remains crucial. Existing tools used to conduct molecular analysis are all based on the principle of biopsy i.e. taking samples of more or less whole cells or tissues which are then analysed ex situ. These techniques therefore deteriorate biological integrity; in addition, they cannot always be used especially as the very insertion of a sampling device must be minimal in some areas, in particular in the brain.

DESCRIPTION OF THE INVENTION

The invention, in one of its aspects, sets out to overcome the drawbacks of existing sampling devices.

Molecular imprint is a novel approach. It consists no longer of extracting tissues from the area of interest, but simply of applying the sampling tool thereto. By contact, on a suitable associated surface, numerous molecules such as proteins come to be trapped on the tool and can then be desorbed and analysed ex situ.

The invention therefore proposes using mere contact to sample molecules of biological interest: an imprint of the tissue is obtained on a device of the invention, and the molecules collected in this manner in a capture zone of the device can then be analysed. In particular, since the device of usually planar shape is of small size, the developed surface area of the capture zone of the device of the invention is increased, which means that the quantity of trapped target molecules is sufficient to permit efficient, subsequent analysis.

The sampling device of the invention therefore comprises a support having at least one molecule capture zone on one face. The capture zone is such that its developed surface area is at least three times larger than its surface as seen from overhead; the ratio between the developed and projected surface areas can reach a factor of twenty and even more.

Having regard to its use, the device of the invention is of limited size and is in particular of <<microtechnological>> size, i.e. its microscopic section, less than 1 mm×1 mm, can be fabricated with microtechnology methods. By <<microtechnological>> is meant in particular that the insertion section of the device of the invention does not exceed 1 mm$^2$ and is preferably included in a cylinder of diameter 800 μm, e.g. it has a parallelepiped section in the order of 300 to 600 μm by 100 to 300 μm.

The support may comprise another capture zone on a face opposite the first face.

Advantageously the device of the invention, on one or both faces, comprises several tiered capture zones i.e. separated by interval zones preferably defined materially. Therefore it is possible to analyse molecules present at different depths in the tissue into which the device is inserted.

Preferably, the device is scored between its different capture zones. For example separating means such as notches obtained by partially etching the support are present in the interval zones.

Various embodiments are provided for the capture zones. The capture zones comprise a bottom wall which may delimit a cavity. To increase the developed surface area, the bottom wall may serve as base for microbeads held in position by a semi-permeable membrane, and/or it may have protuberances.

To fabricate these protuberances, microtechnological silicon etching techniques for example or plastic moulding are possible, so as to create organized networks of square, hexagonal or octagonal columns with sides of 3 to 50 μm or 80 μm, e.g. between 5 and 20 μm, and a height of between 10 and 400 μm, e.g. in the order of 50 μm.

Advantageously, the capture zones are functionalised, i.e. the walls of the support and/or the microbeads are associated with markers, which may carry affinity functions for the molecules of interest or which may be used for saturation of majority species, in which case the use of beads having ligands specific to the majority and minority species is preferred.

The device of the invention is preferably associated with a manipulating rod and a guide sleeve so that it can be accurately positioned inside the tissue to be analysed. In particular, the sleeve may comprise means allowing the capture zones to be placed in contact with the surrounding medium only when the device is in place.

According to another aspect, the invention concerns a method with which it is possible to map or perform differentiated analysis depending on the depth of the target zone. A device having several tiered capture zones is inserted in the tissue to be analysed, contact sampling is performed, and the molecules sampled by the different capture zones are analysed separately.

To carry out the analyses, the capture zones may be separated from each other by cutting the scored sections of the device, or the support of the capture zones may be used in the measuring apparatus.

BRIEF DESCRIPTION OF THE DRAWINGS

The characteristics and advantages of the invention will be better understood on reading the description given below with reference to the appended drawings given for illustration purposes and in no way limiting.

DETAILED DESCRIPTION OF PARTICULAR EMBODIMENTS

Molecular biochemistry e.g. genomics or more especially proteomics, namely the study of protein structures, allows analysis of individual components of interest, in particular of biological interest.

Figure 1:
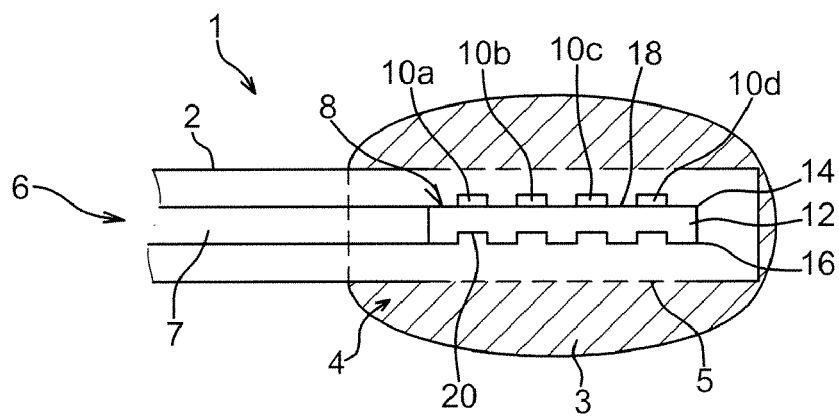
FIG. 1 shows a contact sampling system according to one embodiment of the invention.

Therefore, a sampling system 1 according to the invention, schematised FIG. 1, may comprise a guide sleeve 2 e.g. a catheter: the guide 2 is used inter alia to define the pathway of the sampling device. It may be previously positioned, optionally under optical or radiological monitoring, in the target area 3, a tumour or tissue for example, either in vivo or after collection e.g. by biopsy. Advantageously, the end part 4 of the guide 2 is provided with sealing means 5 which protect the sampling device 6 when it is inserted and allow it to be placed in contact with the tissue of interest 3, once it is in place. Under the invention, the sealing means 5 are preferably located along the longitudinal axis of the guide 2 whose distal end is closed. The sealing means 5 may for example be a rotating or sliding window or a partly resorbable membrane.

The sampling device 6 advantageously comprises a manipulating rod 7 whose length depends on use and the depth of insertion, and which is able to slide within the guide 2. The end part 8 of the rod 7 is intended for the actual sampling operation. Advantageously the guide 2, and hence the manipulating rod 7, are of very small diameter so as not to damage the tissue 3 and to allow non-invasive sampling in a patient. Therefore the diameter of the rod 7 may be limited to a few millimeters, even 100 µm; the outer diameter of the guide 2 is close to the diameter of the rod 7. The rod may be in surgical stainless steel for example.

However, for fine-tuned, accurate analysis of minority compounds present in the area of interest 3, such as molecules, the quantity of fluid sampled must be sufficient to allow extraction of information on tissue type. In particular, the use of an ordinary needle 7 of small diameter does not allow efficient subsequent analysis owing to the small quantity of target molecules trapped on its surface, which has a small surface area even if machined. According to the invention however, the sampling system can be used without restriction, in particular also in the brain, and hence the device 6 is included in a cylinder having a diameter in the order of 995 µm, or even less.

According to the invention, the end part 8 of the sampling device 6 has at least one capture zone 10 whose developed surface area is much greater than the normal surface area, from 3 to over 20 times greater, which makes it possible to reduce the size of the device 6 whilst maintaining sampling in adequate proportions.

The sampling device 6 therefore comprises a support 12 which is preferably independent of the manipulating rod 7 to whose end it may be secured e.g. by gluing preferably with a biocompatible glue. This particularly allows separation of the manufacturing process for each of the two parts, for manipulation and sampling, and also allows the use of a conventional low cost biocompatible rod 7. The support 12 is preferably made in a biocompatible material, silicon in particular, such as specified below; the different component parts of the guide sleeve 2 are also compatible with biological and/or medical use e.g. in gold or plastic, . . . .

The support 12 may be of any shape but is advantageously planar, in wafer form such as described in the methods of fabrication below. Irrespective of its shape, a first face 14 and a second opposite face 16 can be defined on the support 12; if the support 12 is non-planar the terms <<face>> and <<opposite face>> designate portions of the outer surface of the support 12 which are symmetrical relative to a secant plane of the support 12. Advantageously, the faces 14, 16 lie in a support 12 whose length is in the region of 1 to 3 cm long (in the direction of the rod) and whose width is 300 to 800 µm, for a thickness in the order of 200 to 400 µm.

The first face 14 of support 12 is provided with a capture zone 10; it is preferable for the capture zone 10 to leave a free proximal end part 8 that is sufficiently long e.g. 2 to 5 mm, to allow its easy securing to the rod 7. Therefore one preferred embodiment P concerns a rectangular support 12 in silicon of size 300 µm×600 µm×2 cm, the structured zone 10 starting at 3.2 mm away from the edge secured to the rod 7.

Preferably, and such as schematised, several capture zones 10a, 10b, 10c, 10d are present on face 14 of the support 12, separated by interval zones 18. In the example shown, four capture zones are present but evidently their number depends on intended use, in particular on the size of the device 6, on the size of the target area 3 and on the concentration of molecules of interest in this area 3, on the developed surface area of the capture zones 10 and on the fabrication method. Similarly, the interval zones 18 may only be <<virtual>>, i.e. the capture zones 10 merge a priori at macroscopic level, but there are means allowing their distinguishing at microscopic level, and even their separation.

It is also possible for capture zones 20 to be present on the second face 16. Preferably and as illustrated more clearly below, the second capture zones 20 are aligned with and opposite the first zones 10. The second capture zones 20 may be of identical type and geometry to the first zones 10, or they may be different as schematised FIG. 1: the various embodiments presented below may be combined.

Figure 2:
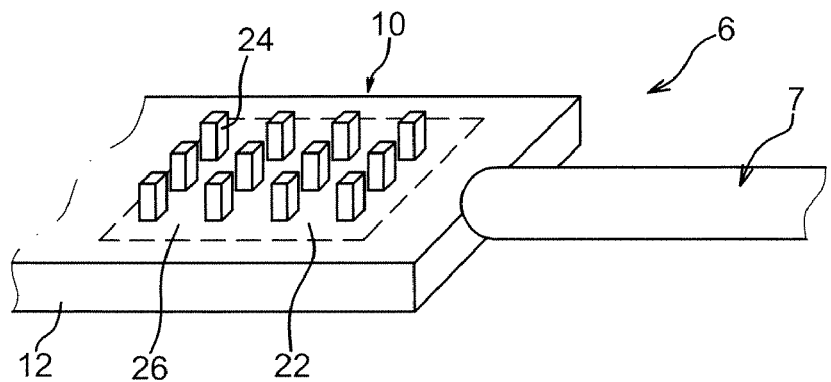
FIG. 2 shows an embodiment of a capture zone for a device according to the invention.

The developed surface area of each of the capture zones 10, 20 is three times greater than the planar surface of the capture zone 10, 20. One embodiment is shown FIG. 2.

The capture zone 10 comprises a bottom wall 22. Depending on fabrication method, the bottom wall 22 may be located on the support 12, or may delimit a cavity therein (see FIG. 4). The bottom wall 22 has a surface s, and has a plurality of protuberances 24. Preferably, if the capture zone comprises a cavity, the height of the protuberances 24 is identical to the depth of the cavity, but it is possible for them to project. Also it is preferable that the surface of the support 12 should be uniform, preferably planar, with the exception of the capture zones 10 and any separating means (described below). Said planar surface can be analysed more easily for example under laser desorption for mass analysis, having regard to the uniformity of impact energy.

The developed surface area S of the capture zone 10 is therefore equal to the surface s of the bottom wall 22 to which must be added the surface area of each of the side walls of the protuberances 24. According to the invention, the surfaces verify the relationship: S>3·s, advantageously factor 3 possibly assuming values of 5 or 10 for example.

Protuberances 24 may assume any desired geometry, for example square columns or columns with hexagonal section. Preferably the protuberances 24 are arranged regularly e.g. in a network with square or hexagonal meshing. According to the preferred embodiment P, the surface structuring is in the form of octagonal studs 24 of silicon, 50 μm de high and 20 or 80 μm wide.

Different fabrication methods can be envisaged for said capture zones 10; for example, if the support 12 is in plastic it is possible to use injection or hot embossing techniques which allow parts to be obtained by replication giving a reverse pattern to previously made moulds. It is therefore possible to manufacture protuberances 24 having sides of 20 μm and a height of 50 μm at low cost, on a support 12 in polyethylene, or polymethyl methacrylate (PMMA), or polycarbonate, or polydimethylsiloxane (PDMS), or Parylene, or Téflon™; one option is also to deposit one of these materials, in particular Parylene or Téflon™, on any plastic even metallic surface in order to make it biocompatible.

If a higher surface/volume ratio is desired, it is possible to use microtechnology techniques. For example, the method described with reference to FIGS. 7 in document FR-A-2 846 957 may be used; the method described in this document however is simplified since only the support 12 is machined: there is no formation of feed channels and/or cover sealing. With said method it is possible to obtain protuberances 24 with sides of 5 μm and a height of 100 μm on a support 12 in silicon. More generally, the protuberances 24 may have sides of 5 to 20 μm (even if sizes of up to 80 or 100 μm are also possible with this method) for a depth of 50 to 400 μm; the machining of the support 12 is such that at the end of the method, the device is biocompatible. In particular, a support 12 in silicon is oxidised so as to be coated with $SiO_2$, having similar biocompatible performance to glass.

Figure 7A:
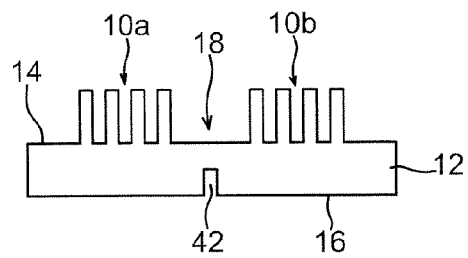
FIGS. 7A to 7E show different embodiments of means to separate the capture zones of a device according to the invention.
Figure 7B:
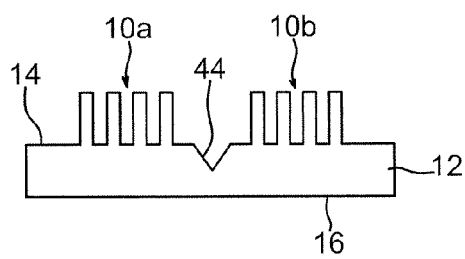
Figure 7C:
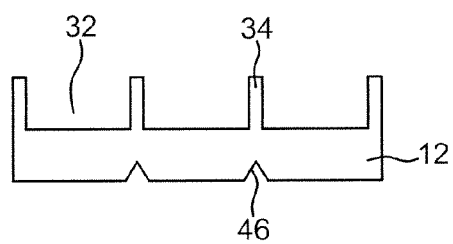
Figure 7D:
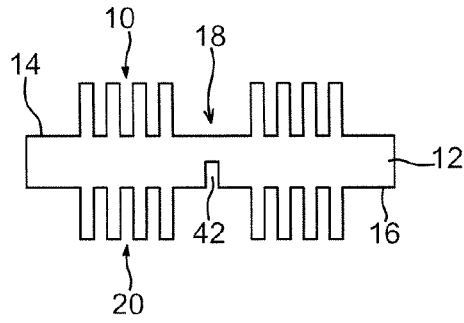

To fabricate capture zones 10,20 on both opposite faces of the support 12, it is possible for example to glue two supports 12, 12' fabricated as previously (see FIG. 7E), or to manufacture a double sided module using microtechnological techniques on silicon, or plastic moulding (FIG. 7D).

In order to further increase the developed surface area of the capture zone 10, it is possible to fill the spaces 26 between the protuberances 24 with microbeads 28. Microbeads 28 are commonly used in microbiology; their diameter is conventionally in the order of ten or so nanometers up to around one hundred microns, and may be made of glass, whether porous or not, allowing them to be functionalised and to remain biocompatible.

Figure 3A:
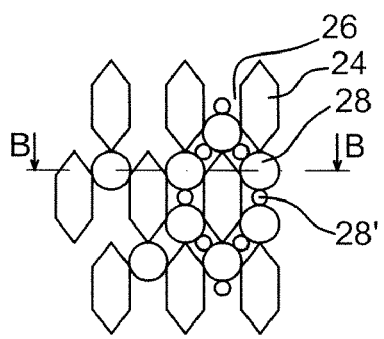
FIGS. 3A and 3B are a cross section of another embodiment of a capture zone for a device according to the invention.
Figure 3B:
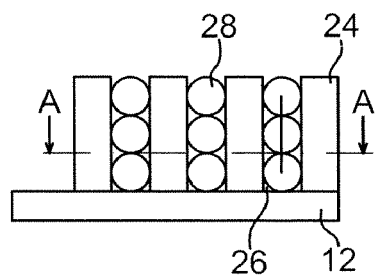

Following the fabrication method of the capture zone 10 and the positioning of the protuberances 24, such as explained in document FR-A-2 846 957, it is possible to arrive at an alignment of beads 28 in spaces 26 between the protuberances 24 (FIG. 3B), which facilitates quantification of the developed surface area. For example, the spaces 26 between the protuberances have a width of less than 50 μm. However any other embodiment is possible, in particular random filling. It is also possible to size the spaces 26 so that first beads 28 are precisely located and second beads 28' of smaller diameter may then be placed in position (FIG. 3A).

In particular, the microbeads 28 increase the developed surface area of the capture zone 10 in remarkable manner. It may be advantageous in this case not to have any protuberances 24, but rather capture zones 30 consisting of cavities 32 filled with beads 28 such as schematised FIG. 4. The cavities 32 of the capture zones 30 may be fabricated by microtechnological etching of the support 12 for example, or by transferring wall meshing 34 or by moulding plastic material. They are then filled with, advantageously calibrated, microbeads 28.

Figure 4:
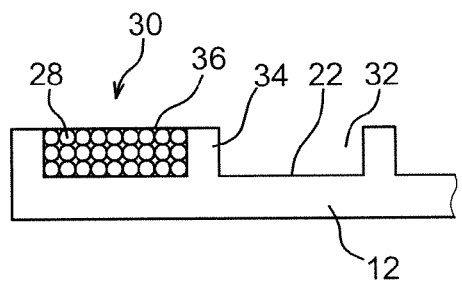
FIG. 4 shows another embodiment of a capture zone for a device according to the invention.

With microbeads as shown FIGS. 3 and 4, it is advantageous to hold the beads 28 in place by a porous membrane 36. The porous film 36 is chosen so as to allow the molecules of interest to migrate inside the capture zone 10, 30. Commercial filters in polycarbonate can be used, having a porosity of less than 1 μm, glued to the cavities by serigraphy (e.g. Dynamask™, by Dynatech), or dry films of photosensitive resin (such as Ordyl™ by Elga) that are insulated by photolithography to achieve porosity; this technique is the best adapted to beads 28 of greater diameter than 1 μm.

It may be of interest to functionalise all or part of the elements of the capture zones 10, 30 in contact with the medium 3 to be analysed, to ensure optimisation of the capture function and/or to target certain molecules of interest. In particular, it is possible to fix a marker on the protuberances 24 and/or beads 28 and/or walls 22, 34.

For functionalisation, the fixing of DNA probes may be considered, or the fixing of specific antibodies, the fixing of an affinity matrix for subsequent analyses by mass spectrometry. For example, it is possible to perform chemical coupling on the device in FIG. 2 having a thick $SiO_2$ oxide on the surface.

It is to be noted that it is possible, in one same capture zone 10,30 to have several different functions by acting either on the fact that the beads and walls are functionalised differently, or on a mixture of beads 28, 28', in particular if their diameter is different, such as described in FR-A-2 846 957.

Figure 5:
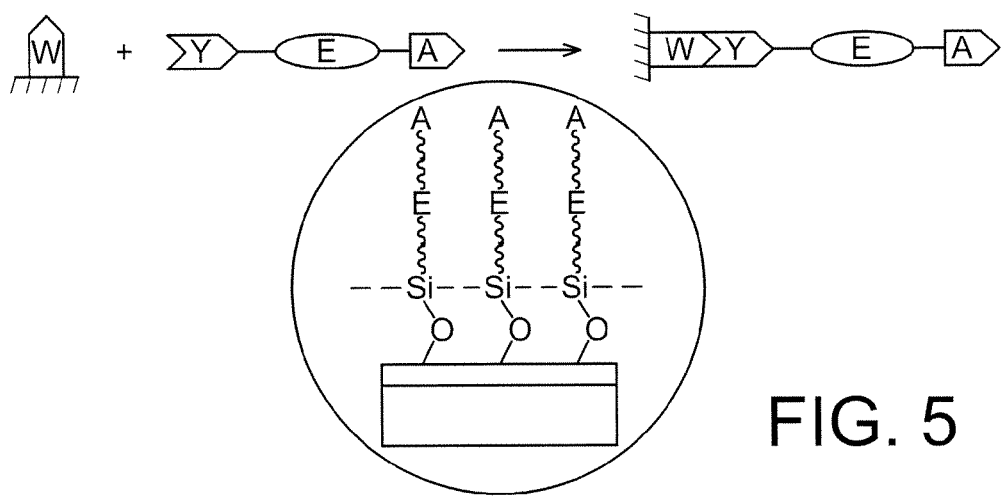
FIG. 5 illustrates functionalisation of the surface of the device.

In particular, regarding the walls 22, 24, 34 of the device, conventionally, functionalisation is made in two or three steps (FIG. 5):

1) Synthesising a bifunctional organic molecule Y-E-A called a coupling agent which will permit non-covalent interface adhesion between the proteins and the organic support.

2) Fixing the coupling agent on the inorganic support 12, which may have been previously treated to obtain a coupling function W (in particular, the 0—Si silylated W function for substrates 12 in silicon coated with a silica oxide layer), by reaction of one of the two Y functions with the surface, the other A function reacting with the protein forming a non-covalent bond.

3) If the terminal function A allowing adsorption of the protein is not able to be synthesized with the silylated function for reasons of chemical incompatibility, the modified support is subjected to one or more post-silanisation reactions until this is obtained.

The coupling function A corresponds to all existing organic and mineral functions such as the functions: $CH_3$, alkenes, alkynes, aryl derivatives, halogens (Br, Cl, I, F), organometal derivatives, alcohols, phenols, diols, ethers, epoxies, carbonylated derivatives (aldehydes, ketones, carboxylic acids, carboxylates, esters, amides, acid chlorides, acid anhydrides), nitrogen-containing derivatives (amines, nitro derivatives, diazo derivatives, imines, enamines, oximes, nitrites), phosphorated derivatives (phosphines, phosphites, phosphates, phosphonates), silicon derivatives, sulfur derivatives (sulfides, dissulfides, thiols, thioethers, sulfones, sulfites, sulfates, sulfonic acids, sulfonates, azasulfoniums), selenium derivatives, . . . .

A spacer group E, used between the two functions A, Y of the coupling agent allows particular properties to be imparted to the film obtained by silanisation. Group E is chosen from among the radicals allowing an organized monolayer to be obtained: a radical E of long chain alkylene type permits an interchain interaction (among the E radicals of alkylene type, particular preference is given to those which have from 8 to 24 carbon atoms); a radical E containing two triple bonds —C≡C— permits cross-linking; a radical E containing a conjugate aromatic chain imparts non-linear optical properties (for example mention may be made of the phenylene-vinylene and phenylene-acetylene radicals); a radical E of pyrrole, thiophene or polysilane type imparts electronic conduction; a radical E of hetero-substituted polyaromatic type imparts photo/electroluminescence properties (e.g. quinones and diazoic compounds); a group E of alkyl or fluoroalkyl type, in particular an alkyl or fluoroalkyl group having 3 to 24 carbon atoms, makes it possible to use the layers obtained by chromatography or electrophoresis.

For functionalisation of the beads, the same principle is used.

Also, it is possible to deposit different types of beads according to sampling areas $10i$, and thereby to obtain a tool having tiered affinity functions A.

Figure 6A:
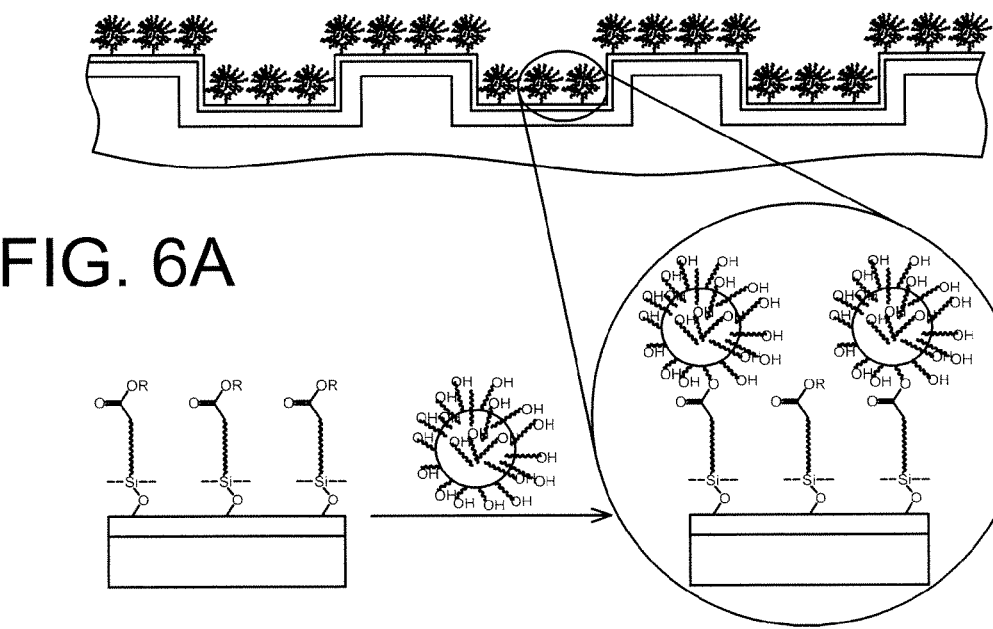
FIGS. 6A to 6C show different types of functionalisation using beads.

For example, for a substrate 12 with a hydrophilic surface such as silanised $SiO_2$, the ester surface functions located on the tool will react with functionalised beads carrying a primary hydroxyl function. After immobilisation of the beads 28, the tool has a developed hydrophilic surface (FIG. 6A).

It is also possible to use the functionalisation of beads 28 to obtain another effect; the increased sensitivity of mass analysis by saturation of the majority species through the use of pools of ligand-carrying beads (dynamic smoothing). For example, if a surface covered by two carrier beads each carrying a ligand specific to a majority protein for the first and a minority protein for the second, is contacted with the tissue, the surface will trap as many majority proteins as minority proteins, which leads to easier detection of this second category during the subsequent analysis phase by mass spectrometry. Majority/minority protein dynamics in nature being 12 log, it is easy to understand the advantage of this approach developed by Ciphergen® on its arrays during the rinsing phase of the sample before deposit on the array. With the device of the invention, it is possible to apply this principle to contact sampling without any subsequent transfer.

Figure 6B:
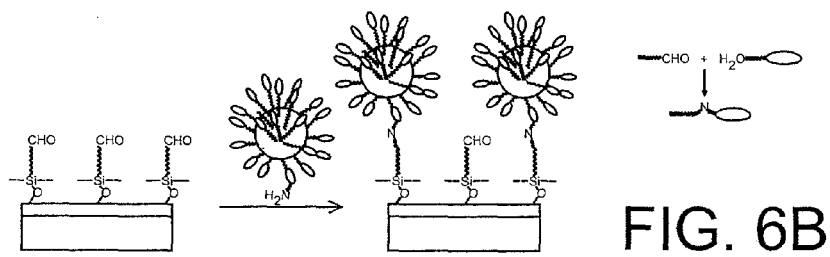
Figure 6C:
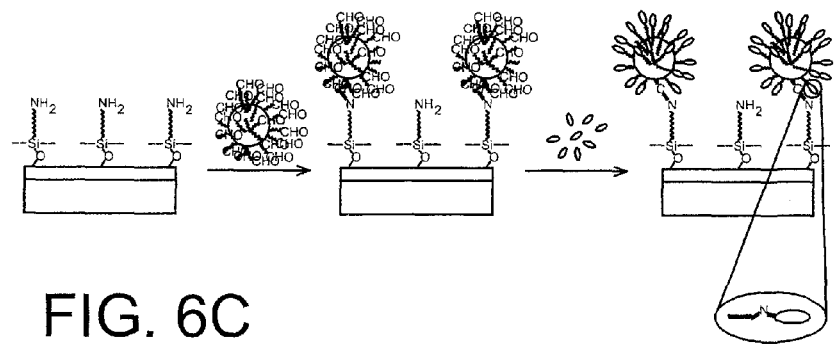

One of the options is to prepare, in n test tubes, n types of bead 28 each carrying a specific ligand, mixing them, then fixing them to the tool via ligand Y ($NH_2$ in FIG. 6B). Another option is to mix n types of specific ligands and to fix them on a tool that is previously functionalised with beads (FIG. 6C).

Also, if the sampling device 6 has several capture zones $10i$ (see FIG. 1), it is possible to use the same functions on each capture zone, or to make spatial differentiation, such as through the <<spotting>> method well known for DNA chips.

Depending on use, and in particular on the analyses conducted on sampled molecules, it may be of interest to separate the capture zones $10a$-$10d$ of one same device 6. In particular the supports 12 may be scored for each of the preceding embodiments.

To facilitate sectioning of the support 12, advantageously the interval zones 18 between the capture zones 10, 30 are provided with separating means. For example, notches may be etched at the same time as the protuberances 24 and/or walls 34 are fabricated: FIG. 7. The interval zones 18, 34 can then easily be sectioned.

Different embodiments can be considered; for example it is possible to initiate cleavage 42 by etching the support 12 on face 16 opposite face 14 comprising the capture zones 10, using a mask and etching for example (FIG. 7A). This notch 44 can also be made on the <<front>> face 14, or isotropic chemical etching may be chosen e.g. using KOH (FIG. 7B).

Regarding devices of the type shown FIG. 4, i.e. with a single cavity 32, usually the interval zones consist of walls 34. It may be desirable in this case also to define cleavage notches 46 on the rear face underneath the walls: FIG. 7C.

Figure 7E:
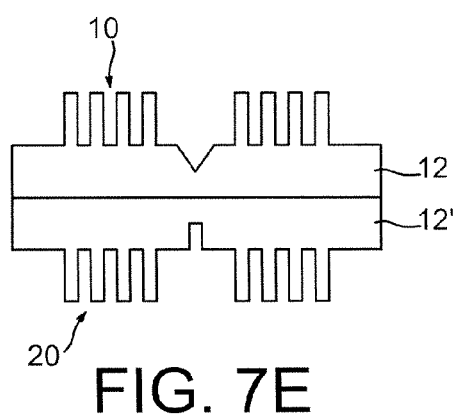

If capture zones 10, 20 are present on each face 14, 16, it is possible to position separating means on only one of the faces (FIG. 7D), or on both (FIG. 7E). Two embodiments can be noted in this respect for devices comprising capture zones 10, 20 on each of their opposite faces 14, 16: one support 12 (FIG. 7D) or gluing of two supports 12, 12' (FIG. 7E).

It is also evident that the different embodiments of notches 42, 44, 46 can be used indifferently and in combination.

According to the preferred embodiment P, a wafer of silicon 100 mm in diameter is machined to obtain 142 end devices after cutting. The support 12 in silicon is advantageously marked: in particular the name of the device, alignment crosses, cutting landmarks, are etched e.g. to 500 nm by photolithography with mask and dry etching.

The rear face undergoes similar treatment (photolithography with mask aligned on the preceding mask, dry etching from 5 to 10 μm, removing the mask resin) to form notches 46. The front face is then patterned and etched for microstructuring, with photolithography and aligned mask, deep dry etching to 50 μm and removal of the resin. The surfaces are then prepared to allow their biological and/or medical use: in particular the polymer (e.g. $C_4F_8$) formed on the sides of the cavities during etching operations is removed by total deoxidation, followed by wet oxidation over 100 nm, then full deoxidation; a final layer of $SiO_2$ is obtained by wet oxidation over 500 nm.

Figure 8:
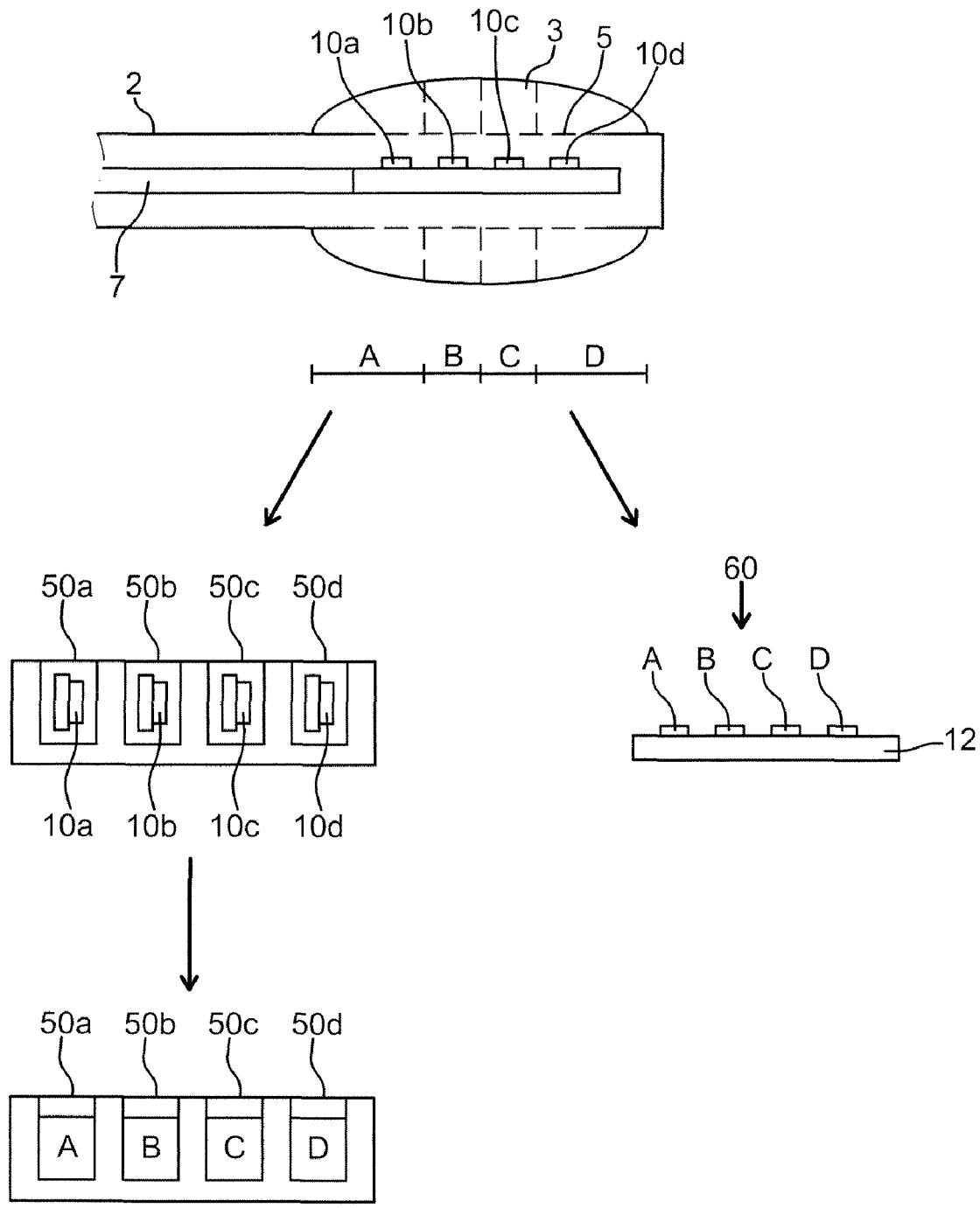
FIG. 8 shows a method of use of a device according to the invention for mapping.

According to one embodiment of use of the device according to the invention schematised FIG. 8, the guide 2 is firstly placed in position, preferably under monitoring, in the target area 3; the support 12 is glued to the end of the rod 7. The rod 7 is inserted in the guide 2 also under optical control to ensure its accurate positioning, and in particular to determine areas A, B, C, D of the tumour 3 corresponding to each of the capture zones $10a$-$10d$. Once the capture zones $10a$-$10d$ are in position, the sealing means 5 are opened and sampling is conducted by affixing; no manipulation of the device itself is required, the contact surface of the capture zones 10 being directly accessible (without the cover for example). This also allows the whole to be miniaturized, the support 12 in particular. The sealing means 5 may then optionally be re-closed. The rod 7 is subsequently removed from the guide 2, the support 12 separated from the guide, and the capture zones $10a$-$10d$ can be analysed.

Two approaches for the treatment of the collected sample can be taken:

1) The device 6 is sectile, and each zone $10a$-$10d$ is separated and treated independently. Once the rod 7 is withdrawn, the support 12 is broken along the score lines and the different zones $10a$-$10d$ are placed in washing and extraction tubes $50a$-$50d$. The extracted molecules A, B, C, D can be stored in a data bank and/or deposited on an array for analysis e.g. a Ciphergen® array used in particular for mass spectrometry for proteomic analysis such as SELDI-TOFF®.

2) It is also possible not to cut the support 12 which therefore maintains the defined, tiered active zones A-D in the tumour 3. It is the support 12 itself which acts as substrate for the end analysis device 60, e.g. by laser assisted direct desorption.

Irrespective of the approach chosen, a map of the tissue of interest can be obtained together with results on protein composition in relation to depth in the target area 3.

The sampling device of the invention therefore has characteristics that are particularly advantageous:

sampling is little invasive; in particular the apparent diameter of the device 6, and even of the system 1 is reduced to a few millimeters, preferably to 1 mm, whilst maintaining a large developed surface area for sufficient capture of target molecules;

sampling is little aggressive: it is made by contact (or <<affixing >>) without cutting tissue 3;

the machined part of the device actually used for sampling is of reduced size and only covers the support 12 which can be associated with a low-cost manipulating rod 7;

the machining of the part used for sampling 12 is reduced to fabrication of the contact zones 10, 20, 30, with no other mechanical elements and no additional cementing or gluing steps;

the large developed surface area of the capture zones 10, 20, 30 compensates for miniaturisation and provides for reliable analyses;

the device 6 can be used for in vivo operations or post-operatively, or even in vitro on sampled tissue requiring molecular analysis;

the presence of tiered capture zones 10a-10d allows analysis, after imprint, of the distribution of molecules of interest in the sampling area 3;

each capture zone 10, 30 can be functionalised according to targeted molecules and/or the type of end analysis (genomics, proteomics);

each capture zone 10a-10d can be separated from the others and can be analysed using a zone specific technique;

the support device 12 can be compatible with any subsequent analysis equipment e.g. it may comprise a specific matrix for mass spectrography;

mapping along the depth axis of the analysed area 3 can be determined according to the successive active zones A-D that are differentiated along the device; the operating method under stereoscopy allows accurate guiding of the device 6 and to determine exactly which area A-D has been probed.

Example of Embodiment

The preceding device P (support 12 in Si 600×300 μm², with octagonal protuberances 24) was silanised then functionalised to yield the carboxylate function. At physiological pH, the biological systems and in particular the proteins are naturally charged; the ion interactions (based on chromatographic principles) can be used for the specific absorption of the protein markers. For the anionic surfaces (negatively charged) carboxylate derivatives are the most frequently used.

The carboxylate and silane functions being incompatible, a strategy of indirect synthesis via the methyl ester of tri-methoxysilylundecan-10-oic acid was chosen.

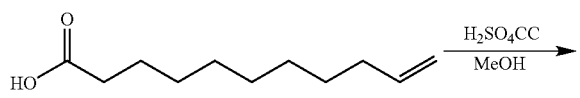

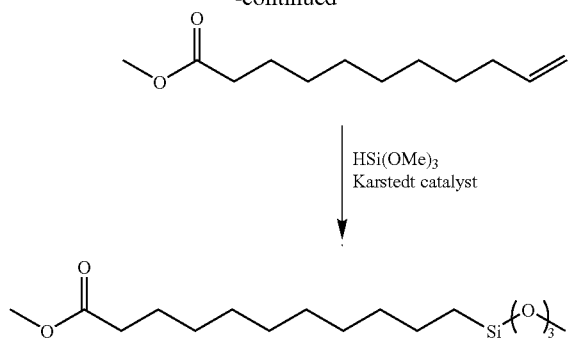

The acid function is protected in the form of a methyl ester after reaction of the undecenoic acid with sulfuric acid and methanol; the incorporation of the silylated group is conducted conventionally via a hydrosilylation reaction.

For example, a methyl ester of 10-undec-1-enoic acid is produced to form the methyl ester of trimethoxysilylundecan-10-oic acid using the following method:

To a solution of undecenoic acid (98%) (10.47 g; 11.5 mL; 56 mmol) dissolved in 500 mL methanol, concentrated sulphuric acid is added (12.88 g; 7 mL; 131 mmol; 2.3 eq.). The reaction is conducted at 0° C. for 4 hours.

After evaporation of the methanol and collection in ethyl acetate, the reaction mixture is successively washed with EDI (×2) and a saturated solution of sodium chloride, dried on anhydrous magnesium sulphate then concentrated to give a colourless liquid (10.99 g; 99%). This gives the following characteristics:

$\delta_H$ (200 MHz; CDCl$_3$): 1.30 (10H; m; H$^{5-9}$)
1.62 (2H; m; H$^4$)
2.04 (2H; m; H$^{10}$)
2.31 (2H; t; H$^3$; $^3J_{H-H}$=7.4 Hz)
3.67 (3H; s; H$^1$)
4.97 (2H; m; H$^{12}$)
5.81 (1H; m; H$^{11}$)
$\delta_c$ (200 MHz; CDCl$_3$): 25.31
29.26
29.42
29.50
29.58
29.66
34.16
34.44
51.76 (C$^1$)
114.51 (C$^{12}$)
139.46 (C$^{11}$)
174.61 (C$^2$)

The methyl ester of 10-undec-1-enoic acid (10.58 g; 53 mmol) is mixed with trimethoxysilane(95%) (8.75 g; 9.1 mL; 68 mmol; 1.3 eq.). The Karstedt catalyst (0.13 g; 0.13 mmol; 0.0025 eq.) is added very slowly. The reaction is conducted at room temperature for 16 hours. The reaction crude is purified by distillation to yield a colourless liquid (120-125° C. at 0.5 mbar; 11.7 g; 70%):

$\delta_H$ (200 MHz; CDCl$_3$): 0.65 (2H; m; H$^{12}$)
1.27 (14H; m; H$^{5-11}$)
1.62 (2H; m; H$^4$)
2.30 (2H; t; H$^3$; $^3J_{H-H}$=7.4 Hz)
3.57 (9H; s; H$^{13}$)
3.67 (3H; s; H$^1$)
$\delta_c$ (200 MHz; CDCl$_3$): 9.21 (C$^{12}$)
22.68

25.04
29.23
29.38 (2C)
29.50 (2C)
33.17
34.19
50.55 ($C^{13}$)
51.46 ($C^1$)
174.38 ($C^2$)
$\delta_{Si}$ (200 MHz; $CDCl_3$): −41.30 (s)

Hydroxylation of the silicon substrate coated with a 500 nm layer of thermal oxide is conducted in a 3.5 M sodium hydroxide solution for 2 hours, with a $10^{-2}$ M silanising solution in anhydrous trichloroethylene, the silanisation reactions being conducted at a controlled temperature of 2° C. for 24 h.

The modified support is contacted with a solution of aluminium iodide to release the carboxylic acid function, which in turn reacts with an aqueous sodium hydroxide solution to give the corresponding carboxylate function.

This device was used for mass analysis of a brain tumour (glioma) obtained after exeresis.

The tissue was affixed to the tool then, after rinsing and depositing on the matrix, analysis was directly performed on the surface.

Figure 9:
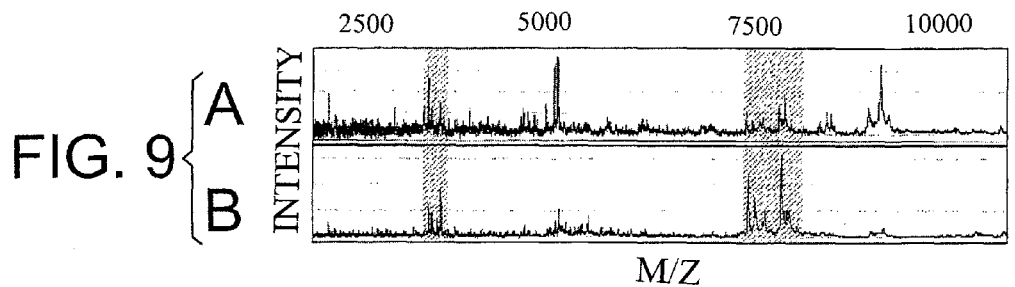
FIG. 9 gives the results of an analysis using a device according to the invention (B) and functionalised (A).

The mass spectra obtained on a SELDI-TOFF, sold under the trade name ProteinChip® System Series 4000 by Ciphergen are shown FIG. 9, the shaded areas representing the majority haemoglobin and transferrin proteins.

It is to be noted that surface chemistry plays a capital role since analysis of surface B without chemistry shows far fewer markers than on the chemically modified surface A (anionic via $COO^-$).

The invention claimed is:

1. A microtechnological sampling device for sampling molecules of biological interest by contact in an in vivo biopsy operation, the device comprising:
   a support having a first face opposite a second face,
   at least one first capture zone on the first face, wherein the developed surface area of the at least one first capture zone is at least three times greater than its surface, and
   a manipulating rod, wherein a one end part of the manipulating rod comprises the support so that the sampling is conducted by said first capture zone.

2. The device according to claim 1, comprising at least one second capture zone on the second face such that the developed surface area of the second capture zone is greater than its surface.

3. The device according to claim 2, wherein the developed surface area of the at least one second capture zone is at least three times greater than its surface.

4. The device according to claim 1, comprising a plurality of first capture zones on the first face separated by first interval zones.

5. The device according to claim 4, comprising a plurality of second capture zones on the second face separated by second interval zones, wherein each first zone being opposite a second zone.

6. The device according to claim 4, comprising separators of the capture zones in the interval zones.

7. The device according to claim 6, wherein the separators are notches on the first and/or second face.

8. The device according to claim 1, wherein the support is in a wafer form.

9. The device according to claim 8, wherein the first and second faces of the support are planar with the exception of the capture zones and, optionally, notches on the first and/or second face.

10. The device according to claim 1, wherein the at least one first capture zone comprises a bottom wall provided with a plurality of protuberances.

11. The device according to claim 10, wherein the support is in plastic.

12. The device according to claim 10, wherein the support is a microtechnological substrate.

13. The device according to claim 12, wherein the substrate is silicon.

14. The device according to claim 10, wherein the height of the protuberances lies between 10 μm and 400 μm, and the surface of the protuberances is between 3×3 μm and 80×80 μm.

15. The device according to claim 10, wherein the protuberances are separated by spaces having a width of less than 50 μm.

16. The device according to claim 10, wherein the protuberances have a hexagonal or octagonal section.

17. The device according to claim 10, wherein the bottom wall and/or protuberances are functionalised.

18. The device according to claim 1, further comprising a guide sleeve for defining a pathway of the sampling device tissue subjected to the biopsy, wherein the manipulating rod is slidable within the guide sleeve.

19. The device according to claim 17, wherein the functionalisation comprises the presence of ligands secured to the surface by a silylated function.

20. The device according to claim 10, comprising microbeads in the spaces between the protuberances.

21. The device according to claim 20, wherein the microbeads are functionalised.

22. The device according to claim 1, wherein the at least one first capture zone comprises a cavity and microbeads arranged in the cavity.

23. The device according to claim 22, comprising a membrane which holds the microbeads in the capture zone.

24. The device according to claim 21, wherein the functionalisation of the microbeads comprises at least two different ligands specific to a majority protein and a minority protein.

25. The device according to claim 18, wherein a diameter of the manipulating rod and the guide sleeve is from a millimeter range to 100 μm.

26. The device according to claim 18, wherein the guide sleeve comprises means for providing a contact of the at least one capture zone and the molecules of biological interest only when the device is in contact with the molecules of biological interest.

27. The device according to claim 18, wherein the guide sleeve comprises means for providing a contact of the at least one capture zone and the molecules of biological interest only when the device is inside tissue to be analyzed.

28. The device according to claim 18, wherein the at least one first capture zone contacts the molecules of biological interest through a rotating or sliding window only when the device is inside tissue to be analyzed.

29. The device according to claim 18, wherein the at least one first capture zone contacts the molecules of biological interest only when the device is inside tissue to be analyzed, through a fixed window in the guide sleeve which is at a distance such that the at least one first capture zone faces the window when the manipulating rod longitudinally abuts the closed end of the guide sleeve.

30. The device according to claim 18, wherein the manipulating rod and the guide sleeve are made of a surgical stainless steel material.

31. The device according to claim 1, wherein the manipulating rod is made of a surgical stainless steel material.

32. A microtechnological sampling device for sampling molecules of biological interest by contact in an in vivo biopsy operation, the device comprising:
a support having a first face opposite a second face, and
at least one first capture zone on the first face such that the developed surface area of the at least one first capture zone is at least three times greater than its surface,
wherein the at least one first capture zone captures the molecules of biological interest during the in vivo biopsy operation.

33. The device according to claim 32, wherein (i) the at least one first capture zone comprises at least one structural feature selected from the group consisting of a protruding structure, a cavity, and a combination thereof, and (ii) the developed surface of the at least one first capture zone includes the bottom surface of the capture zone and a surface area of each of the side walls of the at least one structural feature.

34. The device according to claim 32, comprising at least one second capture zone on the second face such that the developed surface area of the at least one second capture zone is greater than its surface, wherein (iii) the at least one second capture zone comprises at least one structural feature selected from the group consisting of a protruding structure, a cavity, and a combination thereof, and (iv) the developed surface of the at least one second capture zone includes the bottom surface of the capture zone and a surface area of each of the side walls of the at least one structural feature.

35. The device according to claim 32, wherein the developed surface area of the at least one second capture zone is at least three times greater than its surface.

36. The device according to claim 32, wherein the at least one structural feature is a protruding structure.

37. A mapping method for a tissue comprising:
providing the microtechnological device of claim 1,
placing the microtechnological device in the tissue,
contacting the tissue with the capture zones, and
analysing a sample comprising the tissue.

38. The method according to claim 37, further comprising sectioning the device so as to separate the capture zones.

* * * * *

UNITED STATES PATENT AND TRADEMARK OFFICE
CERTIFICATE OF CORRECTION

PATENT NO. : 8,152,736 B2
APPLICATION NO. : 11/814730
DATED : April 10, 2012
INVENTOR(S) : Patrice Caillat et al.

Page 1 of 1

It is certified that error appears in the above-identified patent and that said Letters Patent is hereby corrected as shown below:

On the title page, Item (73), the Assignee's name is incorrect. Item (73) should read:

-- (73) Assignee: **Commissariat a l'Energie Atomique,
Paris (FR)** --

Signed and Sealed this
Twenty-ninth Day of May, 2012

David J. Kappos
*Director of the United States Patent and Trademark Office*